United States Patent [19]

Ohta et al.

[11] 4,227,780
[45] Oct. 14, 1980

[54] EYE EXAMINING INSTRUMENT

[75] Inventors: Shinichi Ohta, Tokyo; Kazunobu Kobayashi; Haruhisa Madate, both of Yokohama, all of Japan

[73] Assignee: Canon Kabushiki Kaisha, Tokyo, Japan

[21] Appl. No.: 918,923

[22] Filed: Jun. 26, 1978

[30] Foreign Application Priority Data

Jun. 29, 1977 [JP] Japan .................................. 52-77449

[51] Int. Cl.² .......................... A61B 3/14; G03B 29/00
[52] U.S. Cl. ........................................... 351/7; 354/62
[58] Field of Search ....................... 351/1, 6, 7; 356/4; 128/660, 745; 354/62

[56] References Cited

U.S. PATENT DOCUMENTS

| 3,850,511 | 11/1974 | Merchant | 351/7 X |
| 3,925,793 | 12/1975 | Matsumura | 351/7 X |

FOREIGN PATENT DOCUMENTS 1127947 6/1955 France .......................................... 351/7

Primary Examiner—John K. Corbin
Assistant Examiner—Rodney Bovernick
Attorney, Agent, or Firm—Fitzpatrick, Cella, Harper & Scinto

[57] ABSTRACT

An eye examining instrument comprises an ultrasonic wave generating source, reflecting members and a receiver. A concave reflecting mirror is provided to direct the generated ultrasonic waves in the direction along the optical axis of the objective lens of the instrument while converging the waves. Also, a concave reflecting mirror is provided to converge the ultrasonic waves reflected upon the cornea of the eye under test and examination into the receiver. The ultrasonic waves received by the receiver are transformed into an electric signal. The electric signal thus produced includes a component informing of the time required to receive the ultrasonic waves after the generation thereof and a component informing of the intensity of the received ultrasonic waves. The time component signal is compared with a reference signal representative of a predetermined working distance between the objective lens and the eye whereas the intensity component signal is compared with a reference signal representative of the alignment of the objective lens with the eye.

13 Claims, 9 Drawing Figures

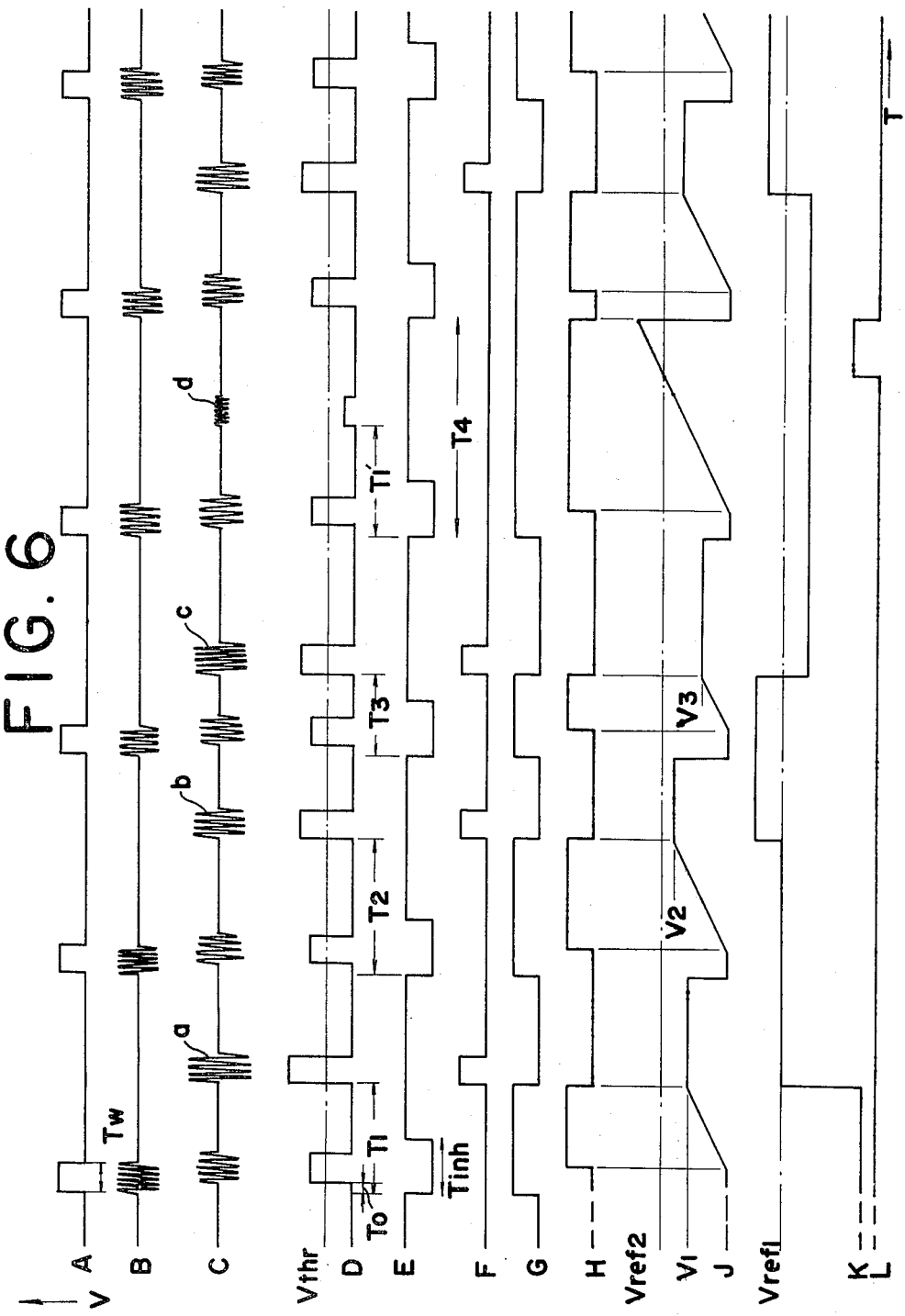

EYE EXAMINING INSTRUMENT

BACKGROUND OF THE INVENTION

1. Field of the Invention

The present invention relates to eye examining and testing instruments and more particularly such eye examining and testing instruments which are provided with a detection system for detecting the positional relation between the objective lens and the eye being examined and tested.

2. Description of the Prior Art

Eye examining and testing instrument are known, for example, which can utilize an eye fundus camera, an eye refractometer and a large ophthalmoscope. In carrying out picture-taking, observation or measurement with such instrument it is essential to correctly set the instrument relative to the eye being examined and tested. In particular, in case of the eye fundus camera, an inaccurate setting of the instrument regarding the working distance and alignment between the objective lens and the human eye causes various troubles such as flare of image due to mixing of a portion of fundus illuminating light reflected upon the cornea into the effective light reflected upon the fundus.

For a conventional fundus camera, adjustment of the working distance has to be made in the following manner:

The examiner initially aligns the optical axis of the objective lens with a human eye to be examined while observing the light illuminating the cornea. When the illumination light becomes correctly incident upon the pupil, an alignment of the optical axis is obtained. Thereafter, the examiner adjusts the working distance while observing through the eyepiece of the instrument whether there is any scattered light or reflected light visible. When no scattered or reflected light becomes visible, there is given the correct working distance. This operation of adjustment must be done repeatedly whenever any change in the positional relation occurs between the objective optical system and the human eye. This is very troublesome and time-consuming.

This problem is further enhanced in case of a non-dilatation type of eye fundus examining instrument. For this type of instrument, invisible light such as infrared rays is used in focusing and adjusting the visual field. Since the examiner can not observe the fundus illuminating light and other harmful lights with the naked eyes, it is impossible to employ the above described procedure of adjustment. Therefore, in case of the use of infrared rays, a higher skillfulness is required for adjustment and the frequency of incorrect setting of the instrument becomes higher.

SUMMARY OF THE INVENTION

Accordingly, it is an object of the invention to provide an instrument of the above mentioned type which enables one to detect whether or not the distance from the eye being examined and tested to the objective optical system is equal to the optimum working distance.

It is another object of the invention to detect whether or not the eye and the objective optical system are in a correct alignment.

It is a further object of the invention to display that the instrument has been correctly adjusted to the optimum working distance and the correct aligned position.

To attain the above objects according to the invention, ultrasonic wave or sound wave generated from the source is directed to the cornea of the eye and the receiver is disposed directed toward the cornea. The receiver receives the wave reflected by the eye and transforms the received wave into an electric signal. The electric signal is compared with a reference signal representative of the optimum working distance as well as with a reference signal representative of alignment. Results of these comparisons are used for alignment of the instrument in the direction of the optical axis and also in the horizontal and vertical directions. When the results are introduced into an auto-positioning system, the necessary adjustment may be carried out automatically, although the following examples show the case wherein the instrument is moved by hand in the optical axis direction and in the horizontal and vertical directions for adjustments.

Other and further objects, features and advantages of the invention will appear more fully from the following description taken in connection with the accompanying drawings.

BRIEF DESCRIPTION OF THE DRAWINGS

FIG. 6 shows various wave forms of outputs appearing at the respective parts of the circuit shown in FIG. 5.

DESCRIPTION OF THE PREFERRED EMBODIMENTS

Figure 1:
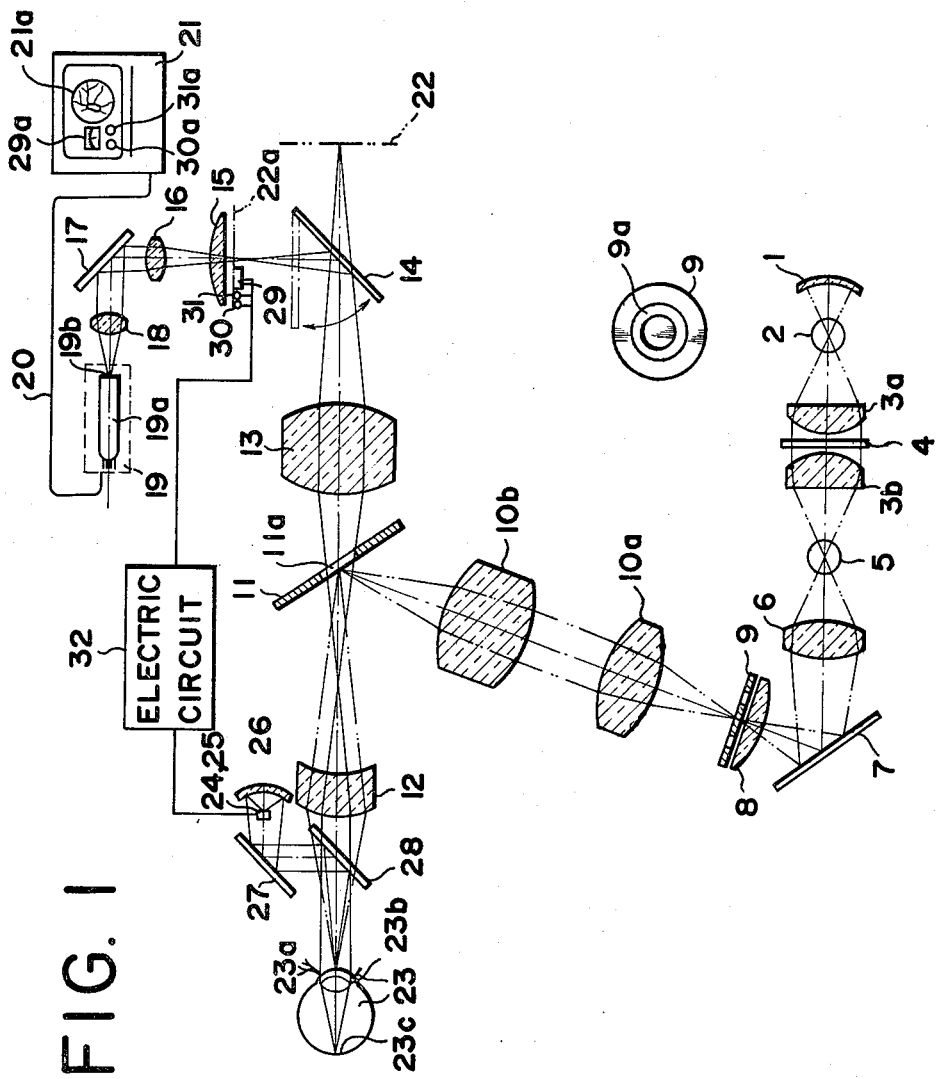
FIG. 1 shows, in longitudinal cross section, an embodiment of the present invention.
Figure 3:
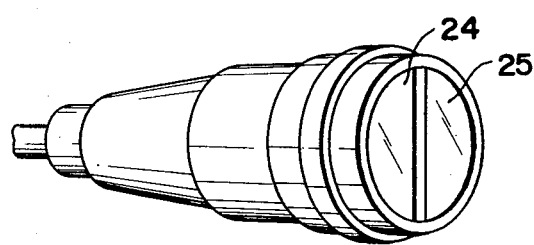
FIGS. 3 and 4 show examples of the combination of sound wave generator and receiver respectively.
Figure 4:
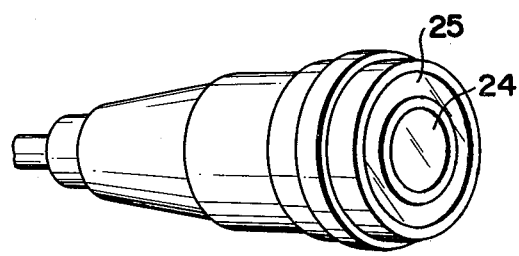

Referring first to FIG. 1 there is schematically shown a non-dilatation type of eye fundus camera in which the present invention is embodied. In the drawing, the reference numeral 1 designates a collector mirror, 2 is an illumination lamp for fundus observation, 3a and 3b are condenser lenses and 4 is a filter which transmits infrared and near infrared rays and cuts off the visible range of light. 5 is a strobo tube, 6 is a second condenser lens, 7 is a light path deflecting mirror, 8 is a field lens and 9 is a ring slit plate having a ring opening 9a therein. Light, whether it is emitted from the lamp 2 or from the strobo tube 5, is focused on the ring slit plate 9. Designated by 10a and 10b are relay lenses, 11 is a bored mirror having a stop opening 11a therein and 12 is an objective lens. The ring slit 9a is once imaged on the bored mirror and then it is again imaged at a predetermined position of eye anterior part of the human eye 23 being tested and examined, for example, at the cornea 23a. 13 is an imaging lens which serves to re-image on the plane of film 22 an image of the fundus formed by the objective lens. 14 is a reflecting mirror disposed movably between its working position where the mirror is placed obliquely in the optical path for observation and its retracted position for taking a picture of the fundus. 15 is a field lens, 16 and 18 are relay lenses, 17 is a light path deflecting mirror, 19 is an infrared television camera, 21 is a television monitor, 19a is a pick-up tube sensitive to the infrared range of light, 19b is a photoelectric surface and 21a is a screen of a cathode-ray tube. Designated by 24 is an ultrasonic wave generator and 25 is an ultrasonic wave receiver. As illustrated in FIGS. 3 and 4, the generator 24 and the receiver 25 are arranged close to each other so as to form together a single unit. 26 is an ultrasonic wave reflecting concave mirror to axis of which extends parallel with the optical axis of the objective lens 12 so as to converge the ultrasonic wave at a predetermined position (optimum working distance of the objective lens) lying on the extension of the optical axis. 27 and 28 are ultrasonic reflecting plates. The reflection plate 27 is disposed inclined at the inclination of 45° relative to the axis of the concave mirror 26 and the other reflecting plate 28 is disposed inclined at 45° relative to the optical axis of the objective lens 12. The reflecting plate 28 is made of such material which reflects ultrasonic waves and transmits light of visible and infrared range. For example, a glass plate or an acrylic plate is used. If necessary, it is designed to be movable at high speed into a position retracted from the light path.

The ultrasonic wave generated from the generator 24 is reflected and converged by the concave mirror 26 and again reflected by the reflecting plates 27 and 28 to converge into the aimed point lying on the extension of the optical axis of the objective lens 12. The aimed point is a point at which the cornea 23a of the eye 23 positioned at the optimum working distance from the objective lens 12 intersects the optical axis of the objective lens.

The ultrasonic wave reflected upon the cornea 23a is reflected by the reflecting plates 28 and 27 successively and then, after reflection by the concave mirror 26, it is converged on the receiver 25.

On an in-air image plane 22a and outside of the path of light reflected upon the fundus there are arranged a meter 29 and luminescence diodes 30 and 31. The meter 29 serves to indicate whether the working distance is correct or not. The diode 30, when it is on, indicates the completion of alignment whereas the diode 31 indicates by its on condition the fact that the instrument is not in alignment.

Designated by 32 is an electric processing circuit of which description will be made later in detail.

With the above described arrangement, when an observation of the fundus is carried out, the light from the illumination lamp 2 together with light reflected by the collector mirror 1 is filtered by the filter 4 interposed between the condenser lenses 3a and 3b. The infrared light transmitted through the filter is introduced into the ring slit plate 9 through lens 6, mirror 7 and field lens 8. After passing through the ring slit 9a, and then through the relay lenses 10a and 10b, the infrared light is reflected to the left as viewed in the drawing by the obliquely disposed bored mirror 11. The reflected light illuminates the fundus 23c of the testing eye 23 passing through the objective lens 12.

Light reflected upon the fundus 23c runs along the same light path but in the opposite direction, namely to the right as viewed in the drawing and passes through the central opening 11a in the bored mirror 11. The light is imaged on the plane 22a through the imaging lens 13 and the turnable mirror 14. The image thus formed is then transferred to the photoelectric surface 19b of the pick-up tube 19a of the infrared television camera 19 through field lens 15, lens 16, mirror 17 and lens 18. The image is transformed into an electric signal and the electric signal is sent to the television monitor 21 via a cable 20. Now, the image of the fundus becomes visible on the cathode-ray tube screen 21a of the television monitor for observation by the examiner.

When a picture of the fundus is taken, the strobo tube 5 is flashed and visible light emitted from it illuminates the fundus 23c travelling the same light path as that for the above described infrared light. The reflected light by the fundus passes under the mirror 14, now turned up to its retracted position suggested by the phantom line, and reaches the film plane 22 which is conjugate with the plane 22a. In this manner, a picture of the image of fundus is taken.

In such a common axis illumination type of eye examining and testing instrument as described above, ring slit 9, bored mirror 11 and cornea 23a should hold a conjugated relation among them in order to prevent any flare from being induced into the picture to be taken or into the observation finder or into the pick-up tube. This is a matter well known to those skilled in the art. To establish the necessary conjugated relation, it is required to keep the distance between the objective lens 12 and the cornea 23a of testing eye at a value particularly determined therefor.

In the above described arrangement, sound waves from the generator 24 are reflected by the concave reflecting mirror 26 and the reflecting plate 27, and then further by the reflecting plate 28 so that the reflected waves have the same axis as that of the above described illumination light for observation or for picture-taking. When ring slit 9, bored mirror 11 and cornea 23a hold the necessary conjugated relation among them, there is also established a conjugated relation between the sound wave generator 24 and the cornea 23a.

The reflected sound wave by the cornea 23a runs along the same path but in the opposite direction to that of the sound wave from the generator, and it enters the sound wave receiver 25 disposed in the vicinity of the generator 24. In the receiver, the received sound wave is transformed into an electric signal which, after being processed in the electric processing circuit 32, drives the meter 29 and the indicators 30, 31 formed, for example, by luminescence diodes. Images of meter 29 and indicators 30, 31 are projected onto the photoelectric surface 19b of the pick-up tube 19a through field lens 15, lens 16, mirror 17 and lens 18 and then transmitted to the television monitor 21 as electric signals via cable 20. Thus, images 29a, 30a and 31a of the meter and indicators are displayed on the screen of the cathode-ray tube of the television monitor 21.

Now, referring to FIGS. 2a–2d showing various positional relations between the cornea 23a and the objective lens 12, the function of the electric circuit shown in FIG. 5 will be described in detail.

Figure 2A:
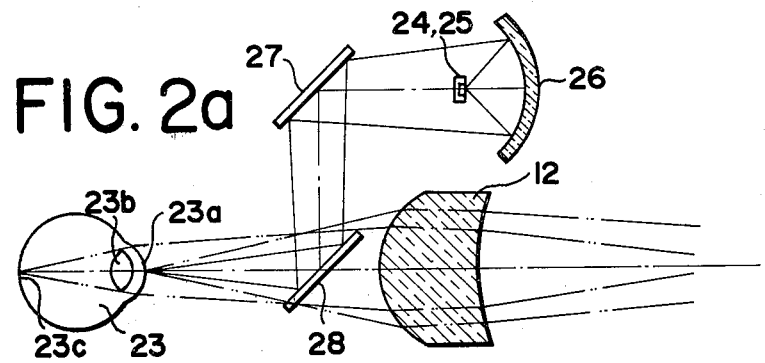
FIGS. 2a–2d show different positional relations between the eye being examined and tested and the objective lens of the instrument.
Figure 2B:
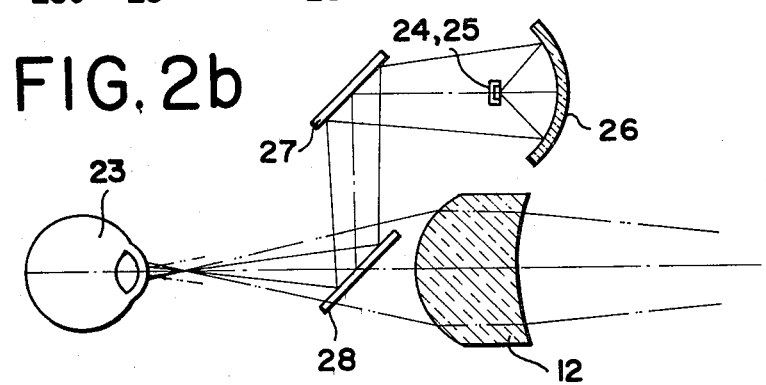
Figure 2C:
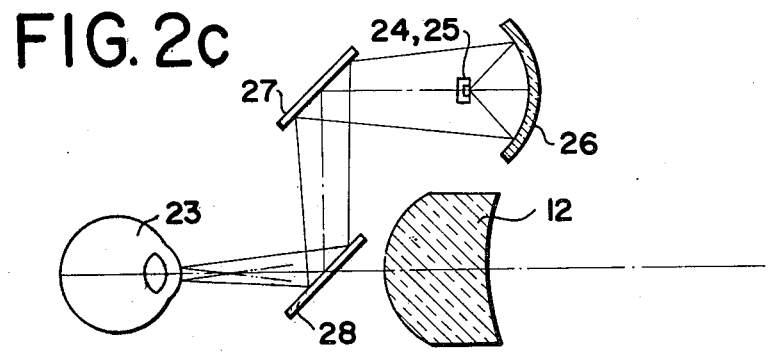
Figure 2D:
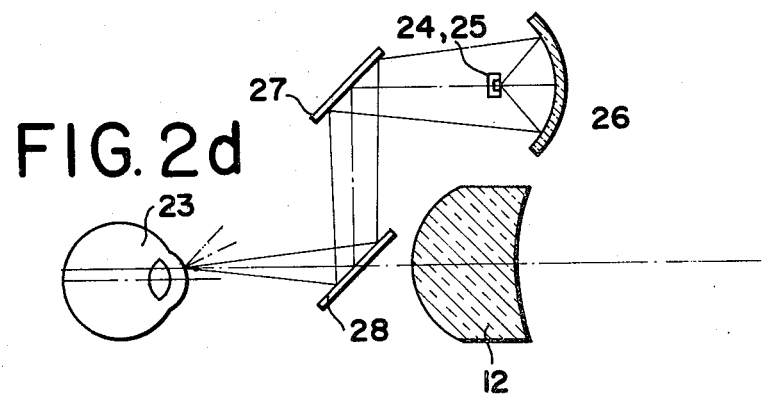

FIG. 2a shows the position in which the cornea and the objective lens are correctly aligned and holds the optimum working distance therebetween. FIG. 2b illustrates the case wherein the distance between the eye 23 and the objective lens 12 is too long although they are in alignment and FIG. 2c illustrates another case wherein the distance between the eye 23 and the objective lens 12 is too short although they are in alignment. In the position shown in FIG. 2d, the eye and the objective lens are out of alignment.

Figure 5:
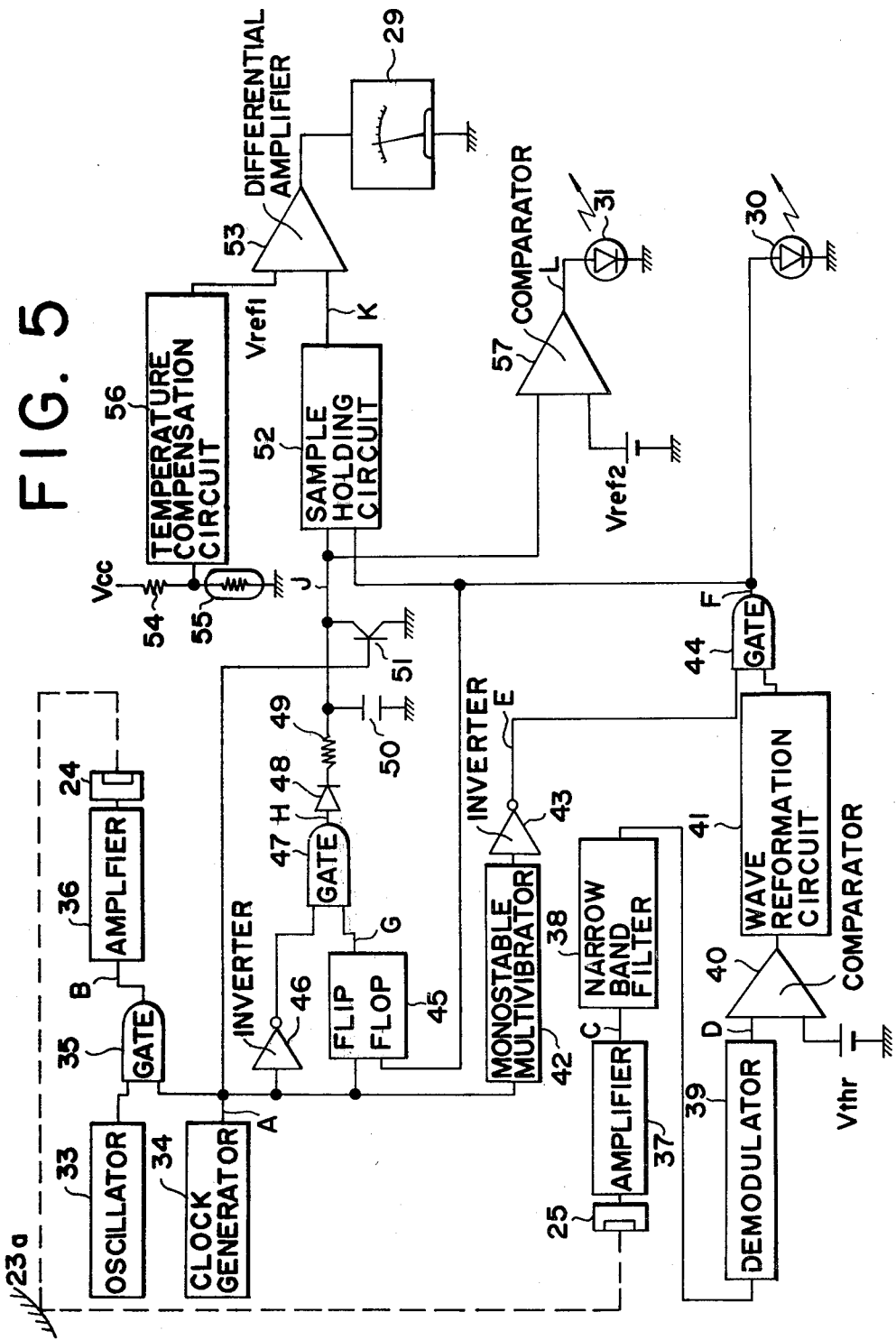
FIG. 5 is a circuit diagram showing an electric processing system used in the invention.

In FIG. 5, the reference numeral 24 is a generator and 25 is a receiver. They are identical with the members 24 and 25 shown in FIG. 1. As will be described hereinafter in detail, the ultrasonic wave received by the receiver 25 is, after being transformed into an electric signal therein, compared with a signal Vthr. The signal Vthr corresponds to the intensity of ultrasonic waves received by the receiver when the eye 23 and the objective lens are spaced from each other by the maximum distance they may have in a common presetting.

If their deviation from alignment is beyond a certain determined limit, then the ultrasonic waves reflected by the cornea 23a can not enter the receiver 25 even after the lapse of a certain determined time or the intensity of ultrasonic waves which could enter the receiver will be very weak. In such case, the zero signal of a gate 44 turns on the luminescence diode 31 through a circuit composed of elements 45 to 51 and a comparator 47. On the contrary, when an output appears at the gate 44, whether the existing working distance is suitable or not can be determined by the time elapsed from the generation of the sound wave to the appearance of output at the gate 44 taking into consideration the velocity of sound variable depending upon the temperature.

The operation of the electic circuit shown in FIG. 5 will be described with reference to FIG. 6.

A signal from an oscillator 33 for sound wave generator 33 is gated at a gate circuit 35 by a signal from a clock generator 34 and them amplified by an amplifier 36 to drive the generator 24. The sound waves reflected by the cornea 23a enters the sound wave receiver 25 which transforms the received sound waves into an electric signal. After passing through amplifier 37, narrow band filter 38 and demodulator 39, the electric signal is compared with an alignment reference signal Vthr in the comparator 40. Only such signal being larger than Vthr passes through a wave reformation circuit 41.

The receiver 25 receives not only the waves reflected by the cornea 23a but also a portion of the waves reflected by the concave reflecting mirror 26 which has to be removed. To remove this portion of the received waves, the output of clock generator 34 drives a monostable multivibrator 42 to form a pulse of Tinh from the rise of output of clock generator 34. The pulse width, Tinh is longer than the sum of pulse width Tw of output from the clock generator and time To which the sound waves generated from the generator 24 and reflected by the concave reflecting mirror 26 takes to enter the receiver 25. The output of the monostable multivibrator 42 is inverted by an inverter 43 so that output from the wave reformation circuit 41 is inhibited by the gate circuit 44 for the time interval of Tinh from the rising point of output from the clock generator 34. Output of the gate 44 has indication element 30 such as luminescence diode put on. Flip-flop circuit 45 is brought into operation by the rising of output from clock generator 34 and is stopped by the rising of output from gate 44. Furthermore, the output of clock generator 34 is inverted by the inverter 46 so as to inhibit the flip-flop from outputting for the time duration of Tw by gate circuit 47. Therefore, the output of gate 47 becomes a pulse the width of which corresponds to the time duration of from the falling of output of the clock generator 34 to the rising of the output of the gate 44. Thus, during this time period it drives an integration circuit constituted of diode 48, resistor 49 and condenser 50. The integration circuit is stopped by a switching element such as transistor 51 for the output pulse duration Tw of clock generator 34.

Sample holding circuit 52 holds the output of the integration circuit, that is, the value of J in FIG. 6 when there is output of the gate 44. The output of the sample holding circuit 52 is put into one input of a differential amplifier 53 the other input of which has a working distance reference signal $Vref_1$. The output of the differential amplifier corresponding to the difference between the two inputs drives a meter 29 which may be a voltmeter. Resistor 54, heat sensitive element 55 and temperature compensation circuit 56 serve to raise or lower the level of the reference signal $Vref_1$ in proportion to atmospheric temperature. When the atmospheric temperature is high, $Vref_1$ lowers and when the atmospheric temperature is low, it rises up. The output of the integration circuit, that is, signal J in FIG. 6 is also compared with a disalignment reference signal $Vref_2$ in the comparator 57. When the signal J is higher than the reference signal $Vref_2$, the indication element such as luminescence diode 31 is turned on.

Wave forms $C(a)$–$C(d)$ in FIG. 6 correspond to the cases $2(a)$–$2(d)$ respectively.

In case of $2(a)$, time required for sound waves generated from the generator 24 to reach the receiver 25 is $T_1$. In case of $2(b)$, it is $T_2$, for $2(c)$ it is $T_3$ and for $2(d)$ it is $T_2'$. Although $T_1'=T_1$ in case of $2(d)$, the eye 23 and the objective lens 12 are out of alignment. Due to this disalignment, the reflected sound wave by the cornea 23a does not travel along the optical axis of the objective lens. It is reflected in a deviated direction suggested by broken line in FIG. $2(d)$ and therefore the reflected wave can hardly enter the receiver 25 as seen in FIG. $6C(d)$ in this case. As a result, when the signal of $C(d)$ is compared with the reference signal Vthr in the comparator 40, it is removed off.

As previously described, the sound wave converging system composed of generator 24, receiver 25, reflecting mirror 26 and reflecting plates 27 and 28 are so arranged that in the position of $2(a)$ there is established a conjugated relation between the generator 24 and the receiver 25. Therefore, in case of $2(a)$, the sound waves received by the receiver 25 have the highest intensity and also the optimum ratio of signal/noise (S/N ratio).

The integration circuit composed of rectifying diode 48, resistance 49 and condenser 50 is brought into operation only for such time duration of subtracting Tw from $T_1$, $T_2$ or $T_3$ to hold the value $V_1$, $V_2$ or $V_3$ respectively until an output comes from the clock 34. In case of $2(d)$, the integration circuit operates for a time given by subtracting Tw from $T_4$ and its output becomes larger than $Vref_2$ (see J in FIG. 6). As a result, a pulse as L in FIG. 6 is produced to put on an alarm device, that is, luminescence diode 31.

In the sample holding circuit 52, $V_1$, $V_2$, $V_3$ are held as shown in FIG. 6-K and the setting for the reference signal is that $Vref_1 = V_1$. Therefore, in case of $V_1$, that is, in case of (a), the meter 29 indicates "0", in case of (b) it indicates "TOO REMOTE" and increase of (c) it indicates "TOO CLOSE". With the change in temperature, the velocity of sound waves varies. If the temperature rises up, then the velocity of the waves sound increases, which results in a reduction of $T_1$ so that $V_1$ may lower. In accordance with this change, the reference signal $Vref_1$ is also lowered by the above mentioned temperature compensation circuit including the elements 54, 55 and 56. When the temperature becomes lower, the apparatus operates in similar manner but in the opposite direction to the above case. Thus, the apparatus is compensated for change of temperature so that in case of (a) the meter 29 always indicates the point of "0".

The examiner watches the images of these indicators 29a, 30a, 31a while observing the image of fundus 21a on the screen of a television set 21. When the meter image 29a on the screen indicates "0", the luminescence diode image 30a turns on and the other diode image 31a is off, then it indicates to the examiner that the eye examining and testing apparatus is now in the optimum position relative to the eye 23.

Instead of meter the and luminescence diode, other indication means such as an acoustic indication also may be used. Also, the use of a combination of visible light cutting off filter and infrared pick-up tube as shown in the above embodiment is not always necessary. A non-dilatation type of fundus camera may be formed also by employing a super sensitive pick-up tube while reducing the quantity of light emitted from the lamp 2 to such extent at which the light does not cause any contraction of pupil of the eye 23.

The application of the invention is never limited only to non-dilatation type apparatus. Rather, the present invention is applicable generally to all common types of ophthalmic instrument and apparatus. However, the most advantageous effect of the invention will be obtained when it is used for non-dilatation type of eye examining and testing instrument.

While the invention has been particularly shown and described with reference to preferred embodiments thereof, it will be understood by those skilled in the art that the foregoing and other changes in form and details can be made therein without departing from the spirit and scope of the invention.

What is claimed is:

1. An eye examining instrument comprising:
   an eye examining system provided with an objective optical means;
   a signal generating source for generating elastic waves;
   a wave projection system for converging the elastic waves to the cornea of the eye which is spaced a predetermined distance from said eye examining system and for directing in a predetermined direction the waves generated by said signal generating source;
   detection means connected with said system for receiving said elastic waves and transforming them into an electric signal;
   a wave receiving system for converging the elastic waves reflected upon the cornea of a human eye onto said detection means; and
   an electric circuit for subjecting said electric signal to a predetermined processing.

2. An eye examining instrument as claimed in claim 1, wherein said wave projection system includes a reflecting member disposed immediately before said objective optical means with its reflecting surface being inclined relative to the optical axis of said objective optical means.

3. An eye examining instrument as claimed in claim 2, wherein said reflecting member reflects said elastic waves and transmits visible light.

4. An eye examining instrument as claimed in claim 2, wherein said reflecting member reflects said elastic waves and transmits infrared light.

5. An eye examining instrument as claimed in claim 1, wherein said wave projection system and said wave receiving system have a common converging reflecting means with its concave surface being directed to said generator and said receiver and a common reflecting plate disposed immediately before said objective optical means.

6. An eye examining instrument as claimed in claim 5, wherein said generator and said receiver are united together.

7. An eye examining instrument as claimed in claim 1, wherein said wave projection system includes a concave reflecting means adapted for converging elastic waves generated from said signal generating source at a predetermined point lying on the extension of optical axis of said objective optical means.

8. An eye examining instrument as claimed in claim 1, wherein said elastic waves are ultrasonic.

9. An eye examining instrument comprising:
   an eye examining system provided with a fixed objective means; a generating source for emitting elastic waves;
   wave reflecting means disposed between said objective means and the eye to be examined for reflecting elastic waves from said generating source toward the eye to be examined;
   a receiver for receiving elastic waves from the eye to be examined and for emitting an electric signal stream; and
   a comparator circuit, connected with said receiver, for comparing said electric signal stream and standard signals relating to a predetermined distance between said objective means and the eye to be examined.

10. An eye examining instrument as claimed in claim 9, wherein said eye examining system is an eye fundus camera system including an observation system and indicating means connected with said comparator circuit is disposed in the light path of said observation system.

11. An eye examining instrument as claimed in claim 9, wherein said wave reflecting means includes a reflecting plate which transmits visible light and infrared light.

12. An eye examining instrument as claimed in claim 9, wherein said wave reflecting means includes a reflecting plate removably disposed immediately before said objective lens.

13. An eye examining instrument comprising:
   an eye examining system, provided with a fixed objective means, for projecting an examining beam on to the fundus of an eye to be examined;
   an ultrasonic generator connected with said eye examining system and directed in a predetermined direction;
   a receiver, connected with said eye examining system and directed in a predetermined direction, for receiving the ultrasonic waves reflected by the cornea of the eye to be examined;
   a comparator electrically connected with said receiver, for comparing a time interval and an intensity detected by said receiver with a time interval and an intensity corresponding to a desired spacing and alignment between said objective means and the eye to be examined.

* * * * *